United States Patent
Costello et al.

[19]

[11] Patent Number: 5,993,439
[45] Date of Patent: Nov. 30, 1999

[54] LENS SHIELD FOR LASER SKIN PERFORATION

[75] Inventors: David J. Costello; Michael A. Wolf; Kenneth G. Schalhoub; Ronald K. Lohrding, all of Albuquerque, N.Mex.; Aleksei Y. Dergatchev, Hoover, Ala.; Warren E. Parkhurst, Moscow, Russian Federation; Valeri G. Polushkin; Sergei A. Kokhanovsky, both of Troitsk, Russian Federation

[73] Assignee: Cell Robotics, Inc., Albuquerque, N.Mex.

[21] Appl. No.: 08/841,005

[22] Filed: Apr. 22, 1997

Related U.S. Application Data

[63] Continuation-in-part of application No. 08/297,295, Aug. 24, 1994, Pat. No. 5,554,153, and application No. 08/675,080, Jul. 3, 1996, Pat. No. 5,908,416, which is a continuation-in-part of application No. 08/297,295, Aug. 24, 1994.

[51] Int. Cl.$^6$ .................................................. A61B 17/36
[52] U.S. Cl. .................................. 606/9; 606/11; 606/16; 606/17
[58] Field of Search ................................. 606/4, 5, 6, 13, 606/14, 15, 16, 17, 10, 11, 12

[56] References Cited

U.S. PATENT DOCUMENTS

| H1673 | 8/1997 | Hanson | 372/35 |
|---|---|---|---|
| 4,648,892 | 3/1987 | Kittrell et al. | 65/4.21 |
| 4,712,537 | 12/1987 | Pender | 128/9 |
| 4,848,323 | 7/1989 | Marijnissen et al. | 128/6 |
| 4,975,581 | 12/1990 | Robinson et al. | 250/339 |

(List continued on next page.)

FOREIGN PATENT DOCUMENTS 591048232  4/1991  Japan .

OTHER PUBLICATIONS

Cutting and Skin–Ablative Properties of Pulsed Mice–Infrared Laser Surgery, Kaufmann et al, 1994, Journal of Dermatological Surgery, pp. 112–118.

A Needle Without A Needle, A Finger Stick Without Sticking A Finger, Tekhnika—Moludezhi, Dec. 1992, with English translation.

(List continued on next page.)

Primary Examiner—Linda C. M. Dvorak
Assistant Examiner—Sonya C. Harris-Ogugua
Attorney, Agent, or Firm—Robert W. Becker & Associates

[57] ABSTRACT

A lens shield system for shielding a laser source of a system used for collecting capillary blood or fluid from skin, the lens shield comprising a strap apparatus releasably emplaceable around a member of a living being, the member having skin thereon and blood therein, and a lens shield member connected to the strap and disposed for receiving and for transmission therethrough of a laser beam from the laser source directed at the skin. A removable lens shield for shielding a laser source of a collection system used for perforating skin and collecting blood or fluid therein or therebeneath, the collection system in a housing, the lens shield comprising a body sized and configured for removable emplacement in the housing of the collection system between the laser source and the skin, and a window in the body through which the laser beam is transmissible prior to contacting the skin. A method for collecting fluid from a living being has been invented which uses the devices mentioned above.

A new laser perforator has been invented for perforating skin with a perforation to permit blood under a surface of the skin to flow out, the perforator in one embodiment having a laser light source for producing an output laser beam, and a mode distribution apparatus for intercepting the output laser beam to control distribution of laser energy of the output laser beam across the perforation of the skin.

17 Claims, 8 Drawing Sheets

U.S. PATENT DOCUMENTS

| | | | |
|---|---|---|---|
| 4,994,060 | 2/1991 | Rink et al. | 606/28 |
| 5,019,075 | 5/1991 | Spears et al. | 606/7 |
| 5,057,099 | 10/1991 | Rink | 606/12 |
| 5,074,861 | 12/1991 | Schneider et al. | 606/17 |
| 5,102,410 | 4/1992 | Dressel | 606/15 |
| 5,165,418 | 11/1992 | Tankovich | 128/760 |
| 5,169,395 | 12/1992 | Narciso, Jr. | 606/7 |
| 5,253,312 | 10/1993 | Payne et al. | 385/31 |
| 5,272,716 | 12/1993 | Soltz et al. | 372/109 |
| 5,290,273 | 3/1994 | Tan | 606/9 |
| 5,292,320 | 3/1994 | Brown et al. | 606/15 |
| 5,298,026 | 3/1994 | Chang | 606/15 |
| 5,352,495 | 10/1994 | Henderson et al. | 427/596 |
| 5,388,987 | 2/1995 | Badoz et al. | 433/29 |
| 5,401,171 | 3/1995 | Paghdiwala | 433/215 |
| 5,432,811 | 7/1995 | Polushkin et al. | 372/66 |
| 5,468,239 | 11/1995 | Tanner et al. | 606/15 |
| 5,486,172 | 1/1996 | Chess | 606/9 |
| 5,496,309 | 3/1996 | Saadat et al. | 606/15 |
| 5,531,738 | 7/1996 | Hessel et al. | 606/2 |
| 5,554,153 | 9/1996 | Costello et al. | 606/9 |
| 5,616,140 | 4/1997 | Prescott | 606/9 |
| 5,643,252 | 7/1997 | Waner et al. | 606/9 |
| 5,653,706 | 8/1997 | Zavislan et al. | 606/9 |
| 5,655,547 | 8/1997 | Karni | 128/898 |
| 5,662,643 | 9/1997 | Kung et al. | 606/3 |
| 5,662,644 | 9/1997 | Swor | 606/9 |
| 5,662,646 | 9/1997 | Fumich | 606/15 |

OTHER PUBLICATIONS

Attention ! New Laser Perforator NTEC 303, Mammology, Jan. 1993, with English translation.

Laser Perforator, USSR Academy of Sciences, Mar. 14, 1991, with English translation.

Laser Perforator—The Device to Get Blood Samples By Non–Contact Method, Denileyko et al, Moscow 1991, Int'l Conference New In Laser Medicine, with English translation.

Basic Explanation of the Experimental Use Of the YAG:ER Laser (Lambda=2.94 Micron) In Skin Plastic Surgery, Denileyko et al, Moscow 1991, Int'l Conference New In Laser Medicine, with English translation.

YAG:ER Laser For Non–Contact Perforation of Skin With the Aim of Investigation of Blood, Denileyko et al, New In Laser Medicine and Surgery, ed. by Skobelkyn, Moscow 1990, with English translation.

Kentek Mini Lase, 1996, pp. 41–42.

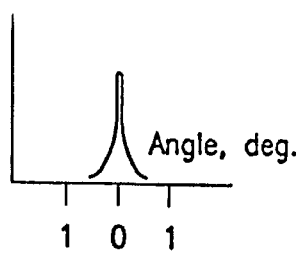
Fig. 9A PRIOR ART
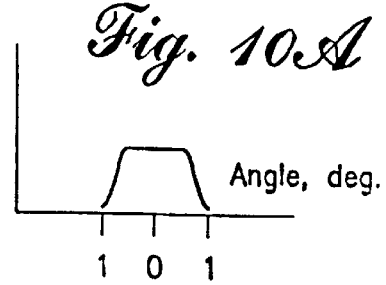
Fig. 10A
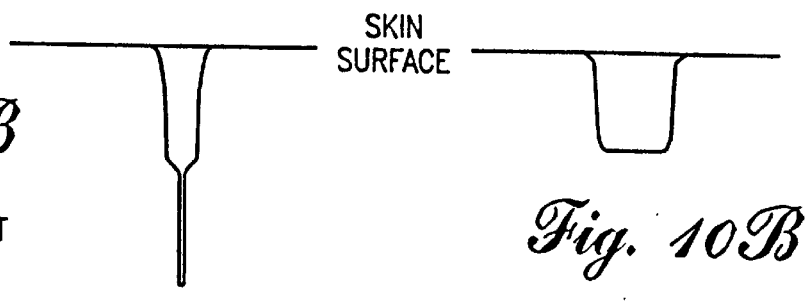
Fig. 9B PRIOR ART
Fig. 10B
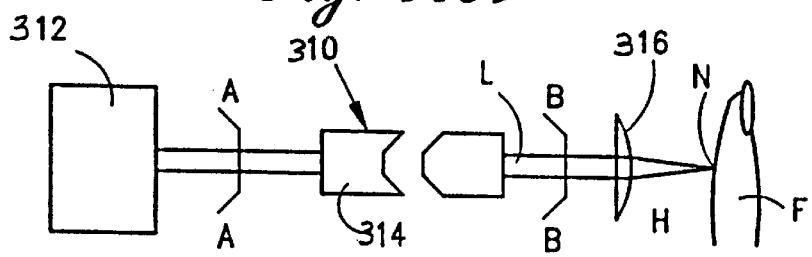
Fig. 11A
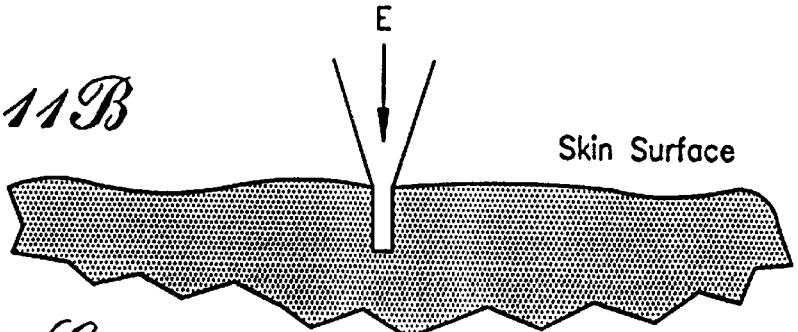
Fig. 11B
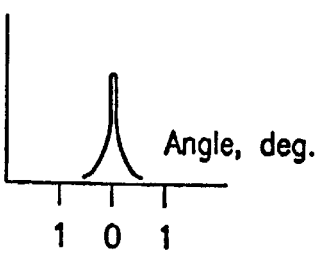
Fig. 11C
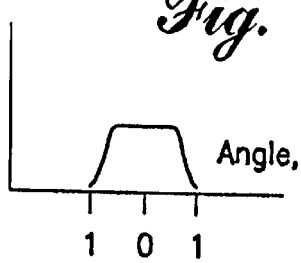
Fig. 11D

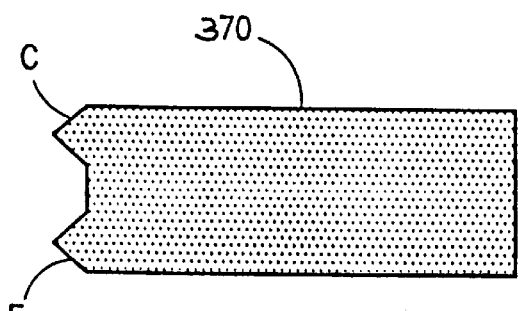
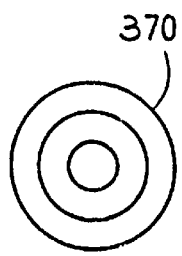
Fig. 16A
Fig. 16B
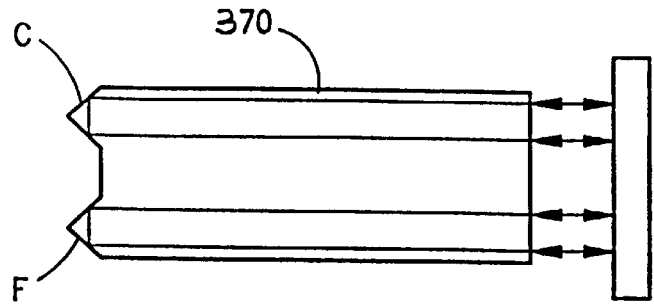
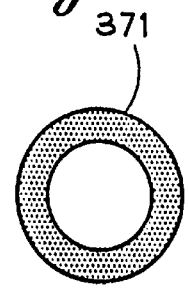
Fig. 16C
Fig. 16D
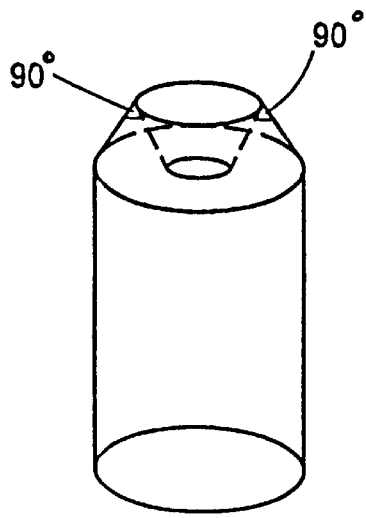
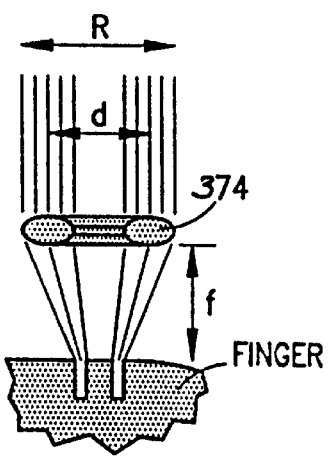
Fig. 17A
Fig. 16E
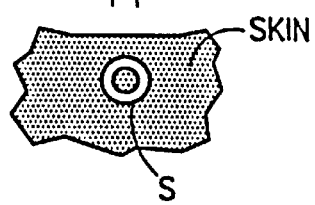
Fig. 17B

LENS SHIELD FOR LASER SKIN PERFORATION

RELATED APPLICATION

This is an continuation-in-part of U.S. Pat. No. 5,554,153 issued Sep. 10, 1996 (U.S. application Ser. No. 08/297,295 filed on Aug. 24, 1994) entitled "Laser Skin Perforator," and U.S. patent application Ser. No. 08/675,080 filed on Jul. 3, 1996 now U.S. Pat. No. 5,908,416 which is a continuation-in-part of U.S. Pat. No. 5,554,153, all co-owned with the present invention and incorporated fully herein.

BACKGROUND OF THE INVENTION

1. Field of the Invention

This invention is directed to a biomedical blood collection device, and, in certain aspects, to laser devices for the collection of capillary blood and/or interstitial fluid. In one aspect this invention is directed to systems for protecting optical and mechanical components from the effects of the byproducts of laser ablation of skin.

2. Description of Related Art

Certain prior art laser skin perforation devices use a pulse or pulses of laser light, generally infrared laser light, to ablate a small hole in the skin of a patient to a depth sufficient to cause bleeding. Small samples of capillary blood may be collected from such small holes for chemical or physical analysis of the blood. International Patent Application No. PCT/US93/10279 discloses certain aspects of laser skin perforation and subsequent capillary blood collection and discusses the potential use of disposable devices for collection of the capillary blood elicited as a result of the procedure.

During the laser perforation process a volume of skin tissue is vaporized by laser energy projected onto the skin surface. The laser energy causes very rapid and explosive heating of the tissue resulting in the formation of a small wound. Ablation gasses are expelled from the wound carrying tissue byproducts. Such expulsion may occur at supersonic speeds such that a popping noise may also be apparent. Ablation gasses may also be heated to the point of luminescence, causing a flash of light to arise from the skin surface. The capillary blood collection procedure is often performed by perforating the fingertips of adult and juvenile patients or by perforating the heels of infant patients.

There are certain negative aspects of certain prior art laser perforation procedures which are a detriment to the performance of perforator devices and to commercial acceptability and success. One such aspect is the expulsion of tissue detritus which may settle onto the surface of a laser lens, reducing the transmissivity of optics and thus requiring frequent cleaning or replacement of the lens. Further, the settling of such detritus on a laser instrument may provide an opportunity for infectious disease transmission when the device is subsequently used by another patient.

Another negative aspect of certain prior art skin perforation procedures is the production of noise and light as a result of skin ablation. These effects may produce undue apprehension in patients experiencing the procedure.

Yet another negative aspect of certain prior art procedures is the possibility that, if blood is spontaneously elicited from the wound as a result of the procedure, such blood may be deposited on the surface of the laser device presenting an opportunity for infectious disease transmission when the device is subsequently used by another patient.

There is, therefore, a need for creating safe, easily replaceable or disposable devices which will serve to minimize these detrimental effects of the laser skin perforation procedure.

SUMMARY OF THE INVENTION

The present invention, in certain aspects, discloses a replaceable or disposable device for use with laser skin perforators which includes a transparent window or lens shield disposed between the skin surface and a proximal optical element of a laser device. Such a window or shield provides a sanitary barrier between the laser device and the patient's skin and wound site. In one aspect such a window or shield is disposable. In another aspect such a window or shield is removable for re-cleaning or sanitizing. In other aspects embodiments of the present invention provide a sealable volume of space around an ablation site which serves to contain physical byproducts and acoustic effects of the ablation process.

In certain embodiments, in order for the laser perforation process to successfully draw blood, the laser light is concentrated into an area of high fluence on the skin surface. It is commonly known that such high energy fluences will damage many common materials and further that absorption of the laser energy such as required to produce such damage will limit the amount of energy available for ablating the skin. Therefore, in certain embodiments of the present invention the window or shield is located at some point in the laser beam path where fluence is sufficiently low so as to control the occurrence of damage to the shield or window.

In one aspect the present invention provides a lens shield device which aids in inserting, removing, and in using the device in a manner that is most acceptable to a human operator.

The present invention, in certain aspects, discloses a lens shield system for shielding a laser source of a system used for accessing capillary blood or fluid from within or beneath skin of a living being, the lens shield having a window through which the laser beam is transmissible, a flange supporting the window, and the lens shield disposable between the laser source and the skin; such a lens shield wherein the window is flat; such a lens shield wherein the laser beam is transmissible through the window substantially without distortion; such a lens shield wherein the flange is configured to space apart the skin and the laser source; such a lens shield wherein the flange extends forming a strap emplaceable around a member of the living being, the member having skin thereon and blood therein; such a lens shield wherein the strap is releasably emplaced around the member; such a lens shield wherein the strap has a strap body with a first and second end, and connection apparatus for releasably connecting the first end to the second end; such a lens shield wherein the connection apparatus includes the first end of the body having an opening therethrough for receiving and releasably holding the second end of the body; such a lens shield wherein the second end of the body has a plurality of spaced-apart flexible ratchet teeth insertable through the opening to facilitate the releasable holding of the second end; such a lens shield with the lens shield member having a body member having an end proximate to the flange and an end distal thereto, projecting away from the flange, and the window in the body member; such a lens shield wherein the window is in the distal end of the body member; such a lens shield wherein the flange is in a plane and the window is substantially parallel to the plane; such a lens shield wherein the flange is in a plane and the window is at an angle to the plane; such a lens shield with adhesive material on the flange for releasably adhering the lens shield to the skin; such a lens shield wherein the flange is a flexible ring for encircling at least a sufficient amount of a body member to hold the lens shield system releasably thereon;

such a lens shield with a multi-part lens shield member which includes a first lens shield member having a hollow body and attachable to the flange, a second lens shield member having a hollow body and connectible to an end of the first lens shield member spaced apart from the flange, and the window disposable between the first and second lens shield members and holdable therebetween by contact of the first lens shield member and the second lens shield member; such a lens shield with a multi-part lens shield member which has a first lens shield member with a first end and a second end and having a hollow body and attachable to the flange, a second lens shield member with a first end and a second end and a hollow body and attachable to the first lens shield member, the window made of flexible material and disposed between the first end of the second lens shield member and the second end of the first lens shield member so that the window is positionable between the laser source and the skin; such a lens shield wherein the flange extends forming a strap emplaceable around a member of a living being and the lens shield has a lens shield member which has a body member having an end proximate to the strap and an end distal thereto projecting from the strap, and the window in the body member.

The present invention, in certain aspects, discloses a removable lens shield for shielding a laser source of a skin perforating system used for perforating skin and accessing blood or fluid therein or therebeneath, the perforation system in a housing, the removable lens shield removably disposable through an aperture in the housing and having a body sized and configured for removable emplacement through the aperture of the housing of the skin perforating system between the laser source and the skin, a window in the body through which the laser beam is transmissible prior to contacting the skin, and a flange supporting the window, the flange disposable between the laser source and the skin and preventing contact of the laser source with the skin.

The present invention, in certain aspects, discloses a lens shield for shielding a laser source of a skin perforating system used for perforating skin and collecting blood or fluid therein or therebeneath, the collection system in a housing, the lens shield having a first lens shield member having a hollow body with a first end and a second end, a second lens shield member with a hollow body and a first end and a second end, the second lens shield member attachable to the first lens shield member, and a window made of flexible material and disposable between the first end of the second lens shield member and the second end of the first lens shield member, the first end of the second lens shield member sized and disposed for receiving therein the second end of the first lens shield member to position the window over the second end of the first lens shield member; and such a lens shield with a ring member for receiving a finger from which blood or fluid is to be collected, the ring member connected to the first end of the first lens shield member.

The present invention, in certain aspects, discloses a lens shield system for shielding a laser source of a skin perforation system used for accessing capillary blood or fluid from skin, the lens shield having a lens shield member disposable for receiving and for transmission therethrough of a laser beam from the laser source directed at the skin, the lens shield member having a first end and a second end, a flange at the first end of the lens shield member for facilitating positioning of the lens shield member on the skin.

The present invention, in certain aspects, discloses a method of making a lens shield for shielding a laser source of a skin perforation system used for accessing capillary blood or fluid from skin, the method including making the lens shield from a single piece of plastic material; such a method wherein the lens shield has a window for transmission therethrough of a laser beam of the skin perforation system; such a method wherein the lens shield is made by a molding process; such a method wherein the lens shield is made by a thermoforming process; and such a method wherein the lens shield is made by a pressure forming process.

The present invention, in certain aspects, discloses a method of making a lens shield for shielding a laser source of a skin perforation system used for accessing capillary blood or fluid from skin, the method including making a first lens shield member, making a second lens shield member, and capturing a window between the first and second lens shield members, the window disposable for transmission therethrough of a laser beam from the laser source; such a method wherein the making is a process selected from the group consisting of molding, thermoforming and pressure forming; and such a method wherein the first lens shield member is made from a single piece of plastic material, and the second lens shield member is made from a single piece of plastic material.

In various embodiments the present invention discloses certain mechanisms used to insure that laser devices used for skin perforation and capillary blood sampling exhibit a high order mode distribution which improves the performance of such perforator devices. These mechanisms are effected by manipulation of beam conditioning optics and of the resonator of solid-state lasers.

The present invention provides evenly distributed laser energy across a wound site, producing a more closely regulated wound with respect to diameter and depth. Obtaining access to capillary blood with this system provides a less painful sensation to the patient and better control of the wound profile with respect to previously disclosed laser-based skin perforators. Evenly distributed energy across a greater set of modal vectors produces a more controlled wound profile. In certain embodiments of the present invention, control over the mode distribution of a laser beam is achieved by the following: a) optimization of the geometry of laser resonator geometry; b) use of external spatial filters; or c) use of optical fibers and waveguides. Projecting a laser beam with high mode distribution on skin according to the present invention produces an upper wound profile with a relatively broad bowl portion without production of the lower, less useful, portion of a wound. Such laser perforator systems also produce less pain among subjects. Incorporation of mode distribution allows greater control of a wound profile and collection of blood, while producing less pain in subjects. Any suitable laser may be used according to the present invention; including, but not limited to, solid-state lasers, gas lasers, dye lasers, diode lasers, and diode-pumped solid-state lasers. In one aspect the output laser beam has an energy level ranging between about 0.1 to about 2 Joules and in one particular aspect the energy level is about 1 Joule. In certain aspects a pulsed laser beam is used with a pulse width ranging between 50 and 500 microseconds.

According to certain embodiments of the present invention, a laser perforator system is designed to control the mode distribution of an output laser beam or has apparatus for the mode distribution of a laser beam, including but not limited to, a hollow waveguide, a solid optical fiber waveguide, spatial filters, specific laser active element geometries, and specific laser active element materials.

Laser light projected into the interior of a hollow waveguide (such as a capillary tube, miniature metal tube, or optical fiber) is reflected from the walls of the waveguide producing a modal distribution which expands along the length of the waveguide. Thus, optical fiber waveguides generate expanded modal distributions of light beams. Optical fibers are designed so that light reflecting from the walls is effectively retained within the fiber. It is possible to guide light through the fiber in such a way as to generate higher order modes. Bends in the optical fiber may be used to generate or reject specific portions of the modal distribution, especially higher order modes, allowing control of the output distribution.

Spatial filters reduce the amount of energy traveling in particular cross sectional areas of a laser beam. Usually, low order modes are reduced by filtering the center of the beam. The use of spatial filtering, however, reduces the overall energy of a beam, reducing the energy efficiency of a system.

It is common knowledge that one design feature of laser devices is the modal distribution of the output beam. In many cases of laser design the designer tries to produce a very low order distribution of modes, including designs of value in other fields which produce a single mode output. It is not obvious that one should reverse the objectives of common laser design practices in order to produce a more useful laser perforator.

Modal distribution of laser output may be manipulated by changes in the geometry of the laser active element. For example the laser element described in U.S. patent application Ser. No. 08/204,560, entitled "Laser", filed on Mar. 1, 1994 and co-owned with the present invention (incorporated herein by reference for all purposes) describes a solid state laser crystal geometry which produces an output with a relatively higher order multi-mode distribution. In general, the inclusion of reflective surfaces into the laser cavity which are not orthogonal to the optical axis of the laser system design, will produce increased order of modal distribution.

It has been found that certain laser materials naturally produce higher order mode distribution. For example, a laser constructed with erbium-doped Yttrium Scandium Aluminum Garnet (YSAG) active element has a higher order distribution than the same laser built with erbium-doped YAG (YAG:Er).

In certain embodiments the present invention discloses devices as discussed above with apparatus for producing a laser output beam with a ring profile yet still preserving multimodal distribution rather than single mode.; in one aspect a hollow cylindrical rod accomplishes this. A system according to this invention includes such apparatus and a laser light source.

In an optical resonator electromagnetic fields can exist whose distribution of amplitudes and phases reproduce themselves upon repeated reflections. These field configurations comprise the transverse electromagnetic modes (TEM) of a passive resonator. Transverse modes are defined by the designation $TEM_{mn}$ for Cartesian coordinates. The integers m and n represent the number of nodes or zeros of intensity transverse to the beam axis in the vertical and horizontal directions. The higher the numbers m and n, the higher the mode order of the beam.

A high order mode distribution for an output beam for certain embodiments of the present invention is defined as any mode distribution characterized with the sum of m and n equal to an integer greater than 0. A high order distribution is, for example, $TEM_{11}$ which resembles the pattern seen with a tetragonal shaped multi-faceted crystal resonator, e.g., see U.S. Pat. No. 5,432,811 co-owned with this invention. (The emission from faceted crystals is actually a combination of modal patterns.) In certain embodiments the mode distributions are characterized by m and n such that the sum of m and n is greater than 1; and, in other embodiments the mode distribution is characterized by a summation of a plurality of modes each characterized by $TEM_{mn}$, where m+n is greater than 0 for each mode.

A ring shaped beam may be created by a resonator operating in single mode (low order) of $TEM_{01}$, but, in certain embodiments of the present invention beam shaping for rings and polyhedrons is achieved by shaping a multi-mode (high order) beam with physical optics, not generated solely by an interface pattern.

DESCRIPTION OF THE DRAWINGS

FIG. 9A is a graph demonstrating low order mode distribution for a prior art laser perforator. FIG. 9B is a schematic representation of a dermal wound produced by a laser with a mode distribution as in FIG. 9A.

FIG. 10A is a graph of high order mode distribution for a laser according to the present invention and FIG. 10B shows schematically a dermal wound produced by such a laser.

FIG. 11A is a schematic view of a laser-based skin perforation system according to the present invention. FIG. 11B is a detail view of the wound-site produced by the perforator system of FIG. 11A. FIG. 11C shows the modal distributions at plane A—A of FIG. 11A. FIG. 11D shows the modal distribution at plane B—B of FIG. 11A.

FIG. 16A is a side view of a laser active element for use according to the present invention. FIG. 16B is an end view of the element of FIG. 16A. FIG. 16C is a schematic representation of the element of FIG. 16A showing the paths of laser light rays. FIG. 16D shows the cross-sectional ring shape of the laser output beam. FIG. 16E is a perspective view of the element of FIG. 16A.

FIG. 17A is a schematic view showing use of a doughnut lens according to present invention. FIG. 17B is a top view of the wound shown in FIG. 17A.

DESCRIPTION OF EMBODIMENTS PREFERRED AT THE TIME OF FILING FOR THIS PATENT

Figure 1:
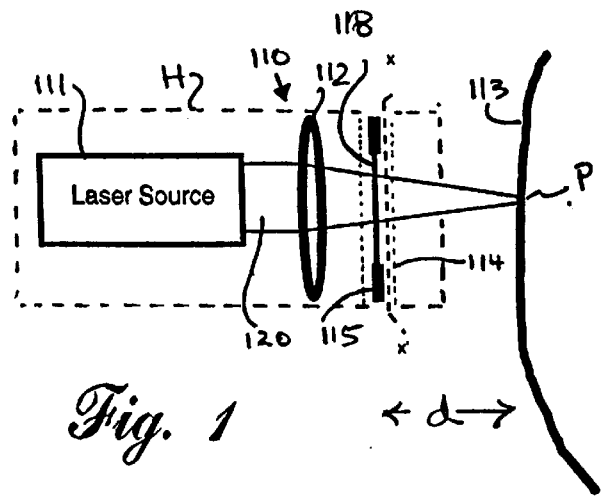
FIG. 1 is a schematic view of a system according to the present invention.

Referring to FIG. 1, a laser perforator device 110 in a housing H, according to the present invention has a laser source 111 which produces a laser beam 120 which is focused through a lens (or lenses) 112 to produce a high energy fluence on a particular section of a skin surface 113. A lens shield 115, having a window portion 118 which is nominally transparent to the laser beam is removably disposed in a slot 114 in the housing and between the lens 112 and the skin surface 113. The lens shield 115 is positioned at a distance "d" from a focal point P of the laser beam so that the energy fluence within the lens shield window 118 (approximately at cross section X–X') is lower than a damage threshold fluence for the window material. Suitable materials for construction of the window include (but are not limited to) glassy or crystalline materials such as glass, sapphire, quartz, fused silica, or calcium chloride. In addition, thin polymer membranes of materials such as polypropylene, polyvinyl chloride, or polysulfone may be used as a window. Alternatively, the window may be placed so that the fluence at cross section X–X' is of a sufficient level to cause some slight damage to the window, insuring that the removable lens shield will be used only once, or a few times at most.

Figure 2:
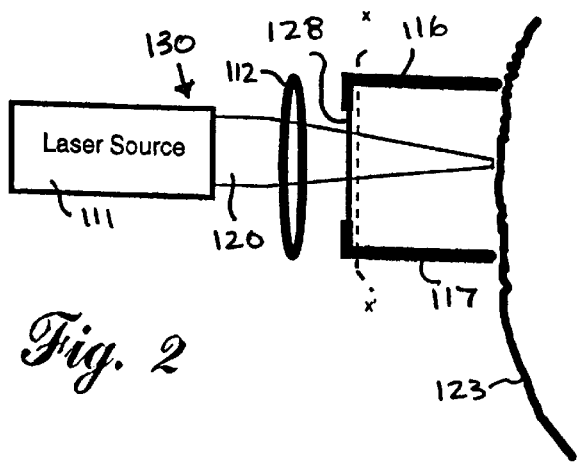
FIG. 2 is a schematic view of a system according to the present invention.

Referring to FIG. 2, a system 130 in a housing, not shown (like the housing H), like the system 110 (like numerals indicate same items) has a lens shield device 116 according to the present invention with a hollow structural member 117 extending from a window 128. The length of the member 117 (as seen from the side in FIG. 2) determines spacing between the window 128 and a skin surface 123. The structural member 117 may be formed so that the skin surface is pressed against the lens shield device 116 sealing a volume of space between the window and the skin. This volume is useful for capturing detritus ejected from the ablation site and also for muffling the sound emitted by the ablation process.

Figures 3A, 3B:
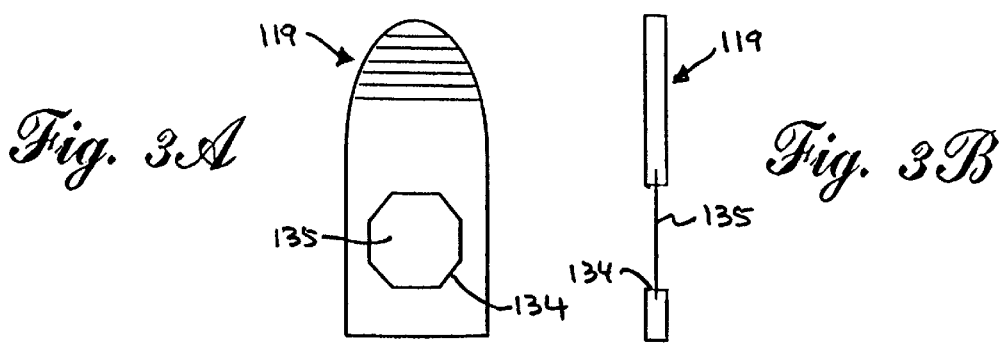
FIG. 3A is a front view of a system according to the present invention.
FIG. 3B is a side view of the system of FIG. 3A.

FIGS. 3A and 3B show an embodiment of a lens shield 119 according to the present invention. The lens shield 119 has a window member 135 mounted in a window 134. The lens shield 119 may be inserted into a laser perforator device through a slot in the laser device housing to position the lens shield 119 between a finger and a laser lens. In one aspect the lens shield is molded from a single piece of material (and may include the window member 115). In another aspect the lens shield 115 is made of flexible material with releasably cooperating fastener material at either end thereof (e.g. VELCRO™ material) for releasably fixation around a finger.

Figure 4:
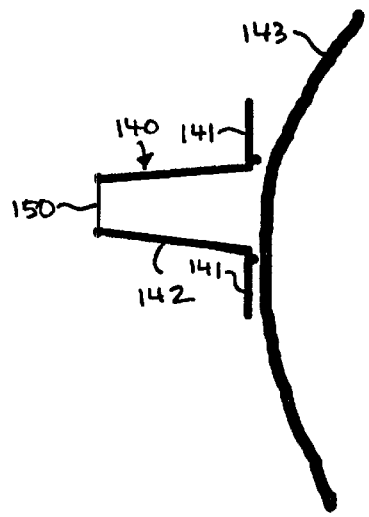
FIG. 4 is a cross-section view of a system according to the present invention.

FIG. 4 shows a lens shield 140 according to the present invention. A generally conical or cylindrical hollow body 142 supports a shield window 150 a distance from a skin surface 143. The lens shield 140 may be inserted into a laser beam path in a direction parallel to a laser beam axis, or it may be inserted through a slot in a laser device housing. Flanges 141 serve to position the lens shield 140 and provide a sanitary barrier between a laser device, not shown, employing the lens shield 140 and the skin surface 143. In certain aspects the shield window 150 is attached to the body 142 or is molded in situ as an integral part thereof. In certain aspects polymer materials (e.g. polypropylene, polyvinylchloride, or polysulfone) are used for shield windows and are molded to approximately 0.001 inches in thickness.

Figure 5A:
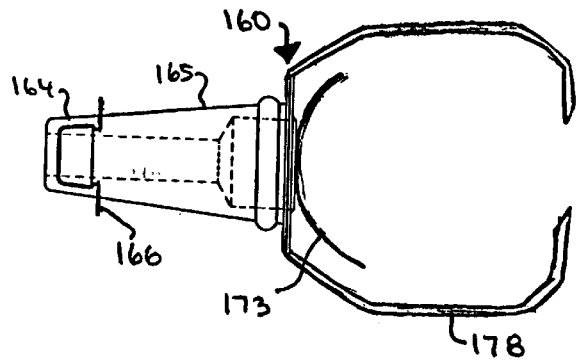
FIG. 5A is a cross-section view of a system according to the present invention.
Figure 5B:
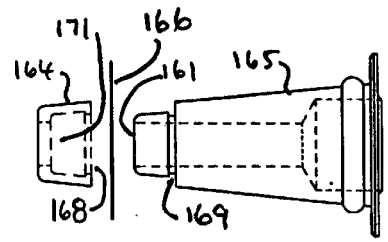
FIG. 5B is an exploded view of the system of FIG. 5A.

FIGS. 5A and 5B shows an embodiment of a lens shield 160 according to the present invention. The lens shield 160 has a first part 164 that holds a thin portion of a stretchable plastic film 166. A second part 165 is inserted into the first part 164 and snapped into place (lip 168 snaps into recess 169) so that the film 166 is stretched over an opening 161 in the second part 165 and an opening 171 in the first part 164. The film 166 thus forms a thin, clear shield window. In one aspect the lens shield 160 is inserted into a slot or aperture in a laser device. The lens shield may be completely pre-built, or it may be partially prebuilt so that the film 166 is stretched immediately prior to use. In one aspect an optional partial ring or flange 178 is connected to the second part 165 to releasably encircle a fingertip or toe to affix the lens shield 160 to a patient. The ring may be a closed ring. Multiple devices with different size rings 178 may be provided to accommodate a variety of different size fingers, members, toes, etc. Alternatively the flange 178 may be closed at one end forming a thimble with a side window for a laser beam. A skin surface 173 (e.g. of a finger or toe) is shown in FIG. 5A.

Figure 6A:
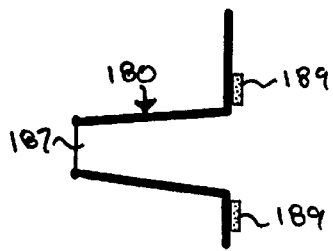
FIG. 6A is a side view of a lens shield according to the present invention.
Figure 6B:
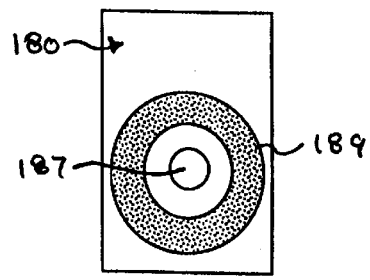
FIG. 6B is a front view of the shield of FIG. 6A.

FIG. 6A and 6B illustrate a lens shield device 180 according to the present invention which may be temporarily affixed to a fingertip, or toe, or skin of a patient so that ablation detritus does not come into contact with other persons until the lens shield device 180 is removed. Adhesive material 189 is secured to a flange 188 of the lens shield device 180 so that the device 180 sticks onto skin.

Figure 7A:
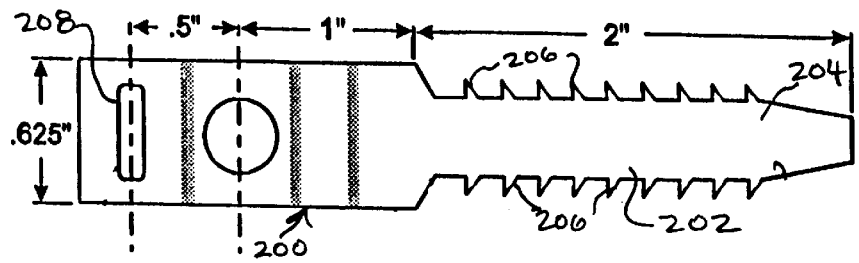
FIG. 7A is a side view of a retaining mechanism for attaching a lens shield to a patient's finger according to the present invention.
Figure 7B:
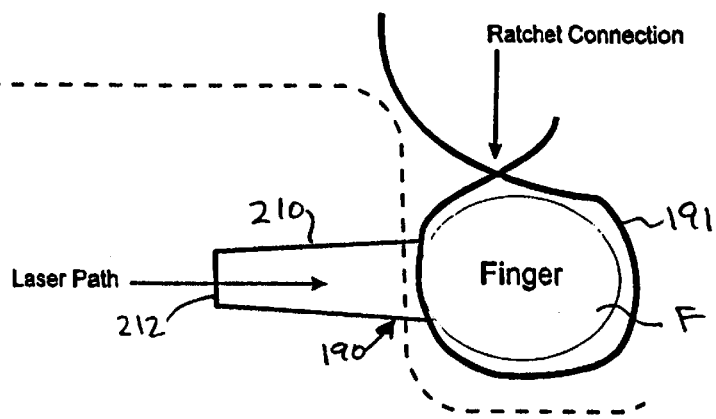
FIG. 7B is a side schematic view of the mechanism of FIG. 7A installed on a finger.

FIGS. 7A and 7B show a lens shield 200 according to the present invention. The lens shield 200 has a flexible strap 202 with a latch piece 204 having flexible ratchet teeth 206. The latch piece 204 is inserted through, and then held in and by, edges of a corresponding opening 208. Any alternative fastener or fastening material may be used whether or not it is a legal equivalent of the latch piece 204 and opening 208. The lens shield has a conical hollow tubular body 210. It is within the scope of this invention for the body 210 to be solid (made of suitable material which is not damaged by a laser or partially solid. A window 212 is mounted at the end of the tubular body. The window may be mounted anywhere in the body so long as the desired optical parameters are maintained. Alternatively the window may be mounted in or on the flexible strap 202 itself and the tubular body 210 deleted. For one particular embodiment of a lens shield 200, dimensions in inches are presented in FIG. 7A.

Figure 8A:
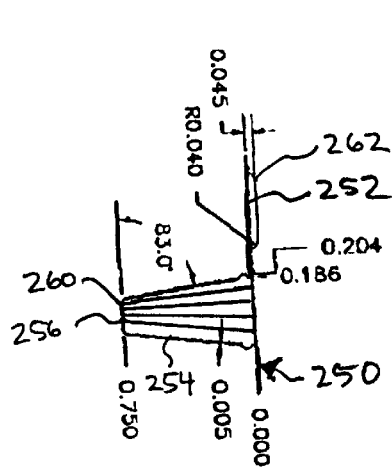
FIG. 8A is a side view of a system according to the present invention.
Figure 8B:
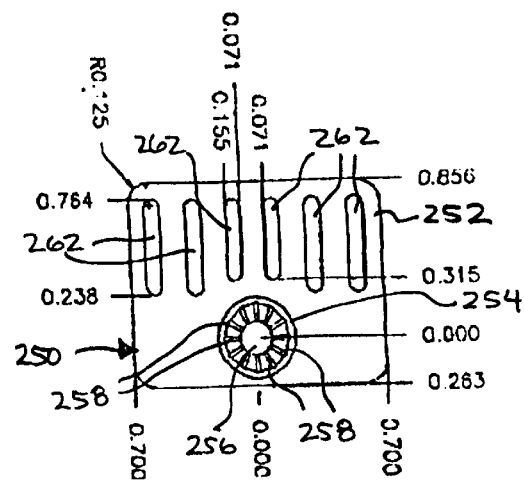
FIG. 8B is a front view of the system of FIG. 8A.

FIGS. 8A and 8B show a lens shield 250 according to the present invention with a flexible strap 252 which may be sized to be wrapped around a finger or sized so that, rather than a strap 252, a body 252 is provided. For one particular embodiment of a lens shield 250 dimensions are presented in FIGS. 8A and 8B in inches; e.g. "0.045" is 0.045 inches and "R 0.040" is a radiused part of 0.040 inches.

A hollow tapered conical member 254 projects from the body 252 and has a window 256 mounted in its end 260 distal from the body 252. The window is shown as perpendicular to an axis of the body in FIG. 8A; but it is within the scope of this invention for the window to be mounted anywhere in the body at any desired angle to the body. The hollow tapered conical member 254 has a plurality of ribs 258 therearound extending from the body 252 to the distal end 260. The ribs enhance rigidity of the member 254. Spaces between ribs may be empty or material may be present between the ribs.

Ridges 262 are provided on the body 262 to facilitate handling thereof, e.g. with fingers and, in one aspect, to facilitate insertion into and removal from a slot in a housing or body. When the lens shield 250 is used by placing it adjacent to or pressing it against skin to be perforated the ridges facilitate such placement and removal therefrom.

Referring to FIGS. 9A and 9B, FIG. 9A shows a graphical representation of a beam profile such as commonly available from laser system designs which do not employ the use of a mode distribution mechanism, as described in the prior art. The vertical axis shows the normalized intensity of the laser and the horizontal axis indicates location in the beam with respect to the axial optical center of the beam ("O"). FIG. 9B shows a schematic representation of the lateral view of holes produced in skin by such lasers as determined by experiments conducted under the direction of the inventors. Normalized intensity shows the relationship of beam intensity versus distance from the beam's axial optical center (O) in arbitrary units. A maximum value for intensity versus distance is 1.

FIG. 10A shows a representation of a beam profile achieved when using a mode distribution mechanism according to the present invention. Again the vertical axis shows normalized intensity. FIG. 10A shows a representation of the lateral cross section of holes in skin obtained when using such a system. The lower portion "stem" portion of the hole is noticeably missing. In addition the relatively broad profile of the hole intersects a greater number of subdermal capillaries, producing more blood availability from wounds of this type, while minimizing the volume of tissue ablated and the sensation of pain to the subject.

Referring now to FIG. 11A, a system 310 according to the present invention has a light generator 312 (e.g. a solid state laser based on YAG:Er, or GGG:Er, or YAP:Er, or other laser with fundamental output wavelength suitable for perforating the skin) and a mode distribution apparatus 314 [e.g. but not limited to a hollow waveguide; a solid optical fiber; or a spatial filter] which produce a laser light beam L which is focused by lens 316 onto a finger F of a patient to produce a hole H which perforates the subdermal capillary bed of the finger and through which the patient's blood may flow for exterior collection.

FIG. 11B shows a schematic representation of a wound in skin produced with the system of FIG. 11A. FIG. 11C shows a representation of the beam distribution profile before the mode distributor at plane A—A of FIG. 11A and FIG. 11D shows the distribution after the mode distributor at plane B—B of FIG. 11A. The vertical axes in FIGS. 11C and 11D are normalized intensity and the horizontal axis represents the optical axis of the beam (center at O).

Figure 12A:
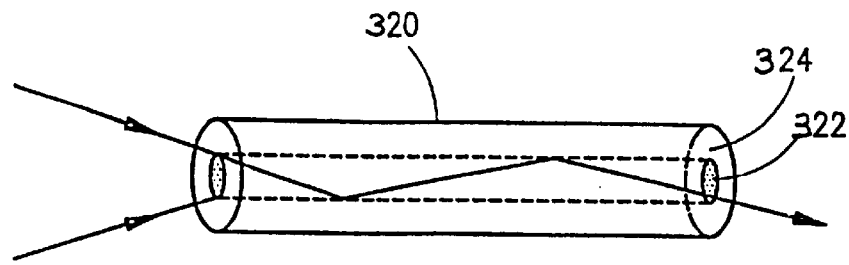
FIG. 12A is a side schematic view of a mode distributor for use according to the present invention.
Figure 12B:
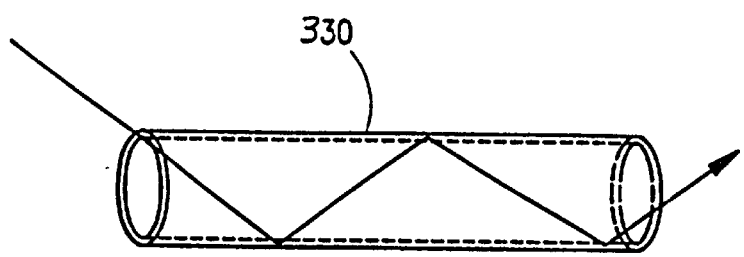
FIG. 12B is a side schematic view of a mode distributor for use according to the present invention.
Figure 12C:
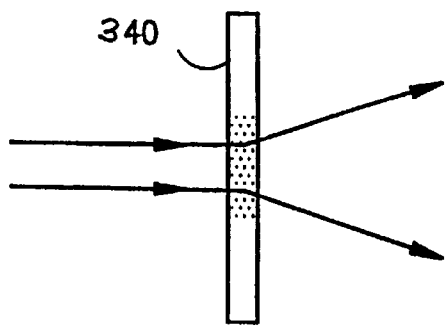
FIG. 12C is a side schematic view of a mode distributor for use according to the present invention.

FIG. 12A shows a mode distributor as an optical fiber 320 with a core 322 and cladding 324. FIG. 12B shows a mode distributor as a light waveguide 330. FIG. 12C shows a mode distributor as a spatial filter 340. In each case multiple reflections of the laser beam (indicated by arrow) incident to the mode distributor result in a higher order mode distribution at the output of the mode distribution mechanism. (Inputs shown on left, outputs to the right in the FIGURES)

Figure 13A:
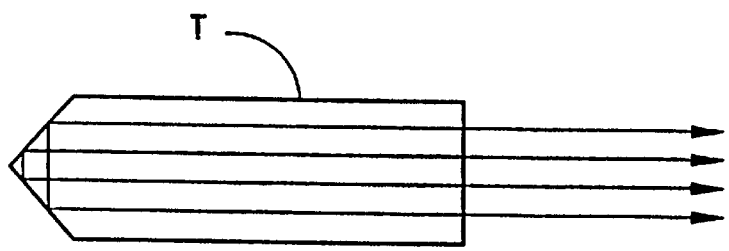
FIG. 13A is a side view of a laser active element for use according to the present invention.
Figure 13B:
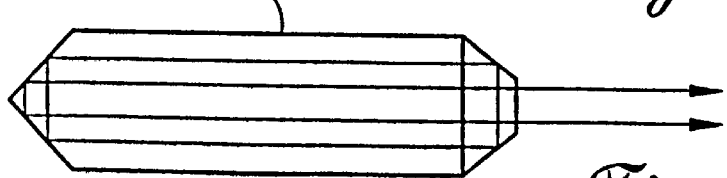
FIG. 13B is a side view of a laser active element for use according to the present invention.

In certain embodiments the light generator 312 includes an active laser element (e.g. but not limited to those described in pending U.S. application Ser. No. 08/204,560) as the element T shown in FIG. 13A. Also, angular reflection surfaces (e.g. as described in but not limited to those of U.S. application Ser. No. 08/204,560) as the element N shown in FIG. 13B may be used in the light generator 312 to increase the modal distribution of the output beam (arrows indicate light paths and reflected light paths).

Figure 14A:
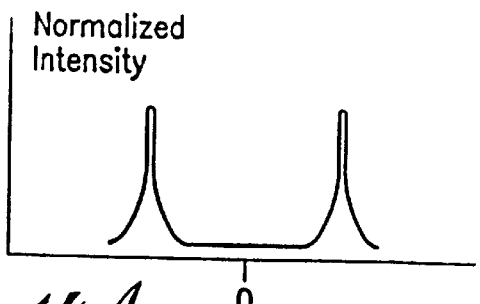
FIG. 14A is a graph of a ring-shaped beam mode distribution for a laser system according to the present invention.
Figure 14C:
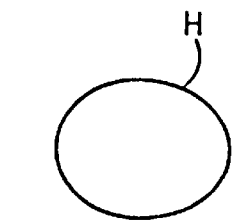
FIG. 14C shows a top-view of the ring shaped wound produced by such a laser system.
Figure 14B:
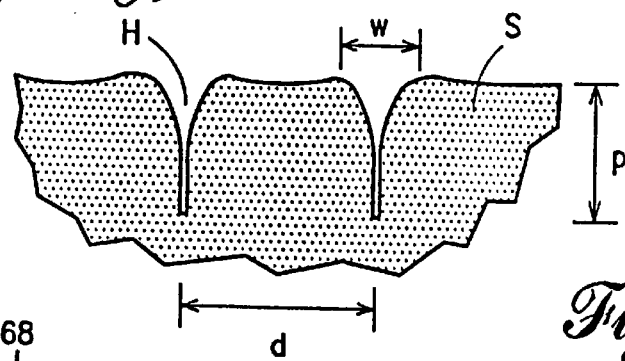
FIG. 14B shows schematically a lateral view of a dermal wound produced by such a laser system.
Figure 15A:
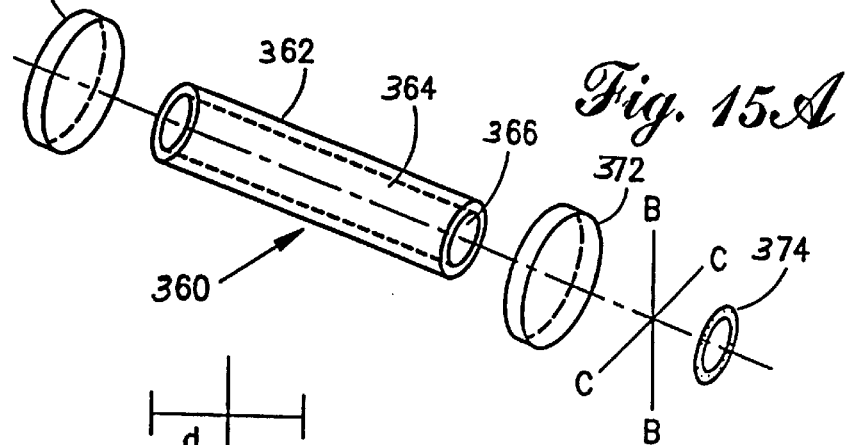
FIG. 15A shows the optical system to produce a laser beam with ring mode distribution according to the present invention.

FIG. 14A illustrates a mode distribution for a laser beam produced with apparatus according to the present invention as shown in FIG. 15A. A hole H in skin S produced by such a beam is shown in FIGS. 14B and 14C. In such an embodiment the modal distribution has a "ring" shape of the output beam so that a circular slit (hole H) is produced in the skin rather than a hole as produced by previously described embodiments. Such slits have been found to be less painful than wider holes. In one particular embodiment a circular slit about 0.05 millimeters wide ("w" in FIG. 14B) is produced with a diameter ("d") of about 0.75 mm, a depth ("p") of about 2 mm, and an outer circumference of about 2.4 mm by a YAG:Er laser operated at about a 1 Joule energy level for about 200 microseconds.

Figure 15B:
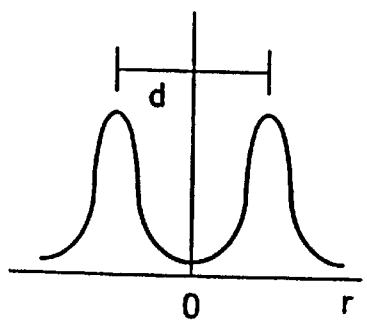
FIG. 15B and 15C show graphs of laser beam energy distribution across axes B—B and C—C of FIG. 15A.
Figure 15C:
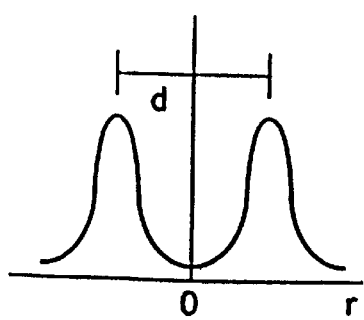

It is within the scope of this invention to provide mode distribution apparatus to produce a ring shaped output beam. FIG. 15A illustrates a solid state laser system 360 for producing a laser beam with "ring" shape according to the present invention. The system 360 has a hollow cylindrical body 364 made, e.g., from YAG:Er, YAP:Er, GGG:Er, YSAG:Er etc. with a central longitudinal channel 366 along its length. Light reflected by a back mirror 368 and a partially reflective mirror 372 is amplified in a hollow cylindrical active laser element 362 producing a "ring" shape laser beam. FIG. 15B is a graph of laser beam energy distribution at axis B—B of FIG. 15A; and FIG. 15C is a graph of laser beam energy distribution at axis C—C of FIG. 15A. "O" in each figure indicates the device' central optical axis.

It is within the scope of this invention that the laser beam energy distribution output profile be asymmetrical with respect to the optical axis of the device and that the energy mode distributions not be identical. FIGS. 16A and 17A show different active elements 370 and 374, respectively, for achieving a high order multi-mode laser beam with a ring shape. Each active element 370 or 380 is not a hollow cylinder but a cylindrical element where one face is made with a cone C which forms a 90 degree reflector (see FIG. 17A) within which a further conical surface F has been ground with an apex diametrically opposed to the cone C such that the two conical surfaces form the circular reflective surface at that end of the element. This reflective surface can also be described as the upper surface of a solid which would be generated by the 360 degree rotation of a right triangle having two equal sides.

FIG. 17A and 17C show an active element 370 for achieving a laser beam with a "ring" shape. The active element 370 is not a hollow cylinder but a cylindrical element with one face made with a cone C which forms a 90 degree reflector (see FIG. 16C) within which a further conical surface F has been ground with an apex diametrically opposed to the cone C such that the conical surface forms the circular reflective surface at that end of the element. The resulting reflective surface can also be described as the upper surface of a solid which would be generated by the 360 degree rotation of a right triangle having two equal sides with the bottom side being less in length or equal to the radius of the laser rod. This annular 90 degree reflector plays a two-fold role: 1) it works like a back mirror, and 2) it determines the back boundary of the resonation cavity of the laser rod. In this design the central part of the rod R is not used to produce a laser beam. Only cylindrical layer limited by the annular corner reflectors produces a laser beam, a beam with a ring shape.

The lens 374 (FIG. 15A, 17A) is used to focus laser beam with the ring shape to decrease the diameter and the thickness of the ring slit in order to make a circular cut in a patient's finger. The lens 374 has a doughnut shape. The diameter d of the lens 374 is determined by the diameter R of the ring shape laser beam (see FIG. 17A). The focal distance f of the lens 374 is chosen preferably to achieve a desired diameter m for the circle slit S on the skin. (See also FIG. 17B.)

Lasers emitting a ring shaped beam may also be used with mode distributions mechanisms as described above to further control the laser system output profile.

Figure 18A:
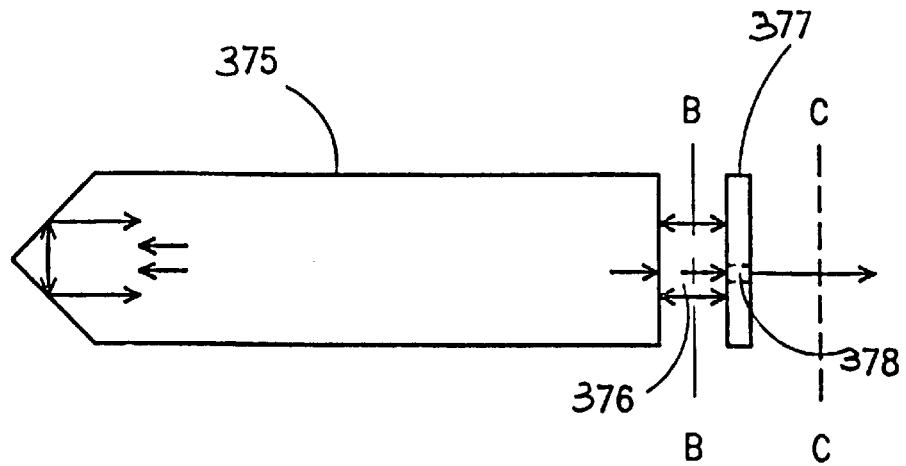
FIG. 18A is a schematic of a system according to the present invention.
Figure 18B:
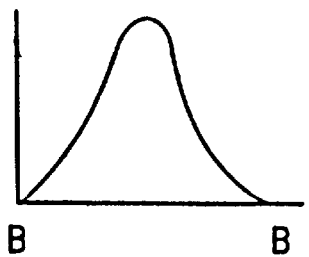
FIG. 18B is a graph of the mode distribution of the beam energy levels of the beam of the device of FIG. 18A along axis of B—B of FIG. 18A.
Figure 18C:
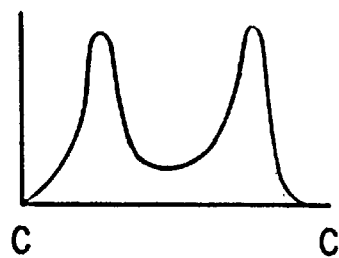
FIG. 18C is a graph of the mode distribution of the beam along axis C—C of FIG. 18A.

FIG. 18A shows another system according to the present invention for producing a ring-shaped laser output profile. In this system a laser rod 375 produces an output beam 376 which is directed toward a mirror 377. The mirror 377 has a hole 378 in it which is preferably centered slightly off the optical axis of the laser system. In this case light impinging on the hole is selected for high-order modes. The output profile of the beam passing through the hole has a ring-shaped profile and produces a ring-shaped wound in skin. FIG. 18B shows the beam's mode at axis B—B of FIG. 18A and FIG. 18C shows the beam's mode distribution at the axis C—C of FIG. 18A. It is within the scope of this invention to provide a hole in the mirror not on the optical axis of the invention at any desired distance from the optical axis.

U.S. Pat. Nos. 5,432,811 and 5,554,113, both co-owned with the present invention, are incorporated fully herein by reference for all purposes.

In certain preferred embodiments of each of the previously described systems and lasers, the laser output beam is pulsed, preferably with a pulse width between 50 and 500 microseconds.

In conclusion, therefore, it is seen that the present invention and the embodiments disclosed herein and those covered by the appended claims are well adapted to carry out the objectives and obtain the ends set forth. Certain changes can be made in the subject matter without departing from the spirit and the scope of this invention. It is realized that changes are possible within the scope of this invention and it is further intended that each element or step recited in any of the following claims is to be understood as referring to all equivalent elements or steps. The following claims are intended to cover the invention as broadly as legally possible in whatever form it may be utilized. The invention claimed herein is new and novel in accordance with 35 U.S.C. §102 and satisfies the conditions for patentability in §102. The invention claimed herein is not obvious in accordance with 35 U.S.C. §103 and satisfies the conditions for patentability in §103. This specification and the claims that follow are in accordance with all of the requirements of 35 U.S.C. §112.

What is claimed is:

1. A lens shield system for shielding a laser source of a system used for accessing capillary blood or fluid from within or beneath skin of a living being, the lens shield comprising a flat window through which a laser beam is transmissible, a flange supporting a body member having an end proximate to the flange and an end distal thereto, projecting away from the flange, wherein said window is disposed in the body member, and a lens shield disposable between the laser source and the skin.

2. The lens shield of claim 1 wherein the laser beam is transmissible through the window substantially without distortion.

3. The lens shield of claim 1 wherein the flange is configured to space apart the skin and the laser source.

4. The lens shield of claim 1 wherein the flange extends forming a strap emplaceable around a member of the living being, the member having skin thereon and blood therein.

5. The lens shield of claim 4 wherein the strap is releasably emplaced around the member.

6. The lens shield of claim 5 wherein the strap further comprises a strap body with a first and second end, and connection apparatus for releasably connecting the first end to the second end.

7. The lens shield of claim 6 wherein the connection apparatus comprises the first end of the strap body having an opening therethrough for receiving and releasably holding the second end of the strap body.

8. The lens shield of claim 7 wherein the second end of the strap body has a plurality of spaced-apart flexible ratchet teeth insertable through the opening thereof to facilitate the releasable holding of the second end.

9. The lens shield of claim 1 wherein the window is in the distal end of the body member.

10. The lens shield system of claim 1 wherein the flange is in a plane and the window is substantially parallel to such plane.

11. The lens shield system of claim 1 wherein the flange is in a such plane and the window is at an angle to the plane.

12. The lens shield system of claim 1 further comprising adhesive material on the flange for releasably adhering the lens shield to the skin.

13. The lens shield of claim 1 wherein the flange comprises a flexible ring for encircling at least a sufficient amount of a body member to hold the lens shield system releasably thereon.

14. A lens shield system for shielding a laser source of a system used for accessing capillary blood or fluid from within or beneath skin of a living being, the lens shield further comprising a multi-part lens shield member which further comprises a first lens shield member having a hollow body and attachable to a flange, a second lens shield member having a hollow body and connectable to an end of the first lens shield member spaced apart from the flange, and a window through which a laser beam is transmissible, said window being disposable between the first and second lens shield members and holdable therebetween by contact of the first lens shield member and the second lens shield member, wherein said multi-part lens shield member is disposable between the laser source and the skin.

15. A lens shield system for shield a laser source of a system used for accessing capillary blood or fluid from within or beneath skin of a living being the lens shield system further comprising a multi-part lens shield member which further comprises a first lens shield member with a first end and a second end and having a hollow body and attachable to a flange, a second lens shield member with a first end and a second end and a hollow body and attachable to the first lens shield member, a window through which a laser beam is transmissible, said window being made of flexible material and disposed between the first end of the second lens shield member and the second end of the first lens shield member so that the window is positionable between the laser source and the skin.

16. A lens shield for shielding a laser source of a skin perforating system used for perforating skin and collecting blood or fluid therein or therebeneath, the collection system in a housing, the lens shield comprising a first lens shield member having a hollow body with a first end and a second end, a second lens shield member with a hollow body and a first end and a second end, the second lens shield member attachable to the first lens shield member, and a window made of flexible material and disposable between the first end of the second lens shield member and the second end of the first lens shield member, the first end of the second lens shield member sized and disposed for receiving therein the second end of the first lens shield member to position the window over the second end of the first lens shield member.

17. The lens shield of claim 16 further comprising a ring member for receiving a finger from which blood or fluid is to be collected, the ring member connected to the first end of the first lens shield member.

* * * * *

UNITED STATES PATENT AND TRADEMARK OFFICE
CERTIFICATE OF CORRECTION

PATENT NO. : 5,993,439
DATED : 11/30/99
INVENTOR(S) : David J. Costello et al

It is certified that error appears in the above-identified patent and that said Letters Patent is hereby corrected as shown below:

Title page, item [75] should read as follows:

[75] Inventors:

David J. Costello, Michael A. Wolf,
Kenneth G. Schalhoub, Ronald K. Lohrding,
Aleksei Y. Dergatchev, Warren E. Parkhurst,
Valeri G. Polushkin, Sergey A. Kokhanovsky Signed and Sealed this Twenty-second Day of August, 2000

Attest:

Q. TODD DICKINSON

Attesting Officer

Director of Patents and Trademarks